(12) United States Patent
Sappey et al.

(10) Patent No.: US 10,352,852 B2
(45) Date of Patent: Jul. 16, 2019

(54) TDLAS ARCHITECTURE FOR WIDELY SPACED WAVELENGTHS

(71) Applicant: John Zink Company, LLC, Tulsa, OK (US)

(72) Inventors: Andrew D. Sappey, Lakewood, CO (US); Bernard Patrick Masterson, Louisville, CO (US)

(73) Assignee: JOHN ZINK COMPANY, LLC, Tulsa, OK (US)

( * ) Notice: Subject to any disclaimer, the term of this patent is extended or adjusted under 35 U.S.C. 154(b) by 19 days.

(21) Appl. No.: 15/538,156

(22) PCT Filed: Nov. 18, 2015

(86) PCT No.: PCT/US2015/061387
§ 371 (c)(1),
(2) Date: Jun. 20, 2017

(87) PCT Pub. No.: WO2016/105704
PCT Pub. Date: Jun. 30, 2016

(65) Prior Publication Data
US 2018/0038788 A1    Feb. 8, 2018

Related U.S. Application Data

(60) Provisional application No. 62/096,426, filed on Dec. 23, 2014.

(51) Int. Cl.
*G01N 21/39* (2006.01)
*G02B 6/35* (2006.01)
(Continued)

(52) U.S. Cl.
CPC ............. *G01N 21/39* (2013.01); *B01D 53/30* (2013.01); *F23N 5/00* (2013.01); *G02B 6/04* (2013.01);
(Continued)

(58) Field of Classification Search
CPC .......... G01N 21/39; G01N 2201/0833; G01N 2201/0826; G01N 21/31; F23N 5/00;
(Continued)

(56) References Cited

U.S. PATENT DOCUMENTS 4,360,372 A   11/1982  Maciejko et al.
4,895,421 A    1/1990  Kim et al.
(Continued)

FOREIGN PATENT DOCUMENTS

CN          1343873        4/2002
CN       101109701 A       1/2008
(Continued)

OTHER PUBLICATIONS

Allen (1998) "Diode laser absorption sensors for gas-dynamic and combustion flows" Measuring Science and Technology 9:5450562.
(Continued)

*Primary Examiner* — Maurice C Smith

(57) ABSTRACT

A system for widely spaced wavelength tunable diode laser absorption spectroscopy includes at least a first and second tunable diode laser generating laser light at a first and second wavelength, wherein laser light of the first and second wavelengths cannot co-propagate efficiently on the same single-mode fiber. A first fiber may be configured to carry light in the first wavelength, and a second fiber configured to carry light in the second wavelength. A fiber bundle may be formed from the distal ends of the first and second fibers stripped of their respective coatings, and arranged with their claddings adjacent to each other. One or more pitch heads are configured to project respective beams of laser light from the fiber bundle through a measurement zone. One or more catch heads located across the measurement zone receive the respective beams and direct the respective beams onto at least one sensor.

20 Claims, 7 Drawing Sheets

(51) Int. Cl.
<table>
<tr><td>G02B 6/36</td><td>(2006.01)</td></tr>
<tr><td>G02B 6/40</td><td>(2006.01)</td></tr>
<tr><td>G02B 6/42</td><td>(2006.01)</td></tr>
<tr><td>G02B 6/04</td><td>(2006.01)</td></tr>
<tr><td>B01D 53/30</td><td>(2006.01)</td></tr>
<tr><td>F23N 5/00</td><td>(2006.01)</td></tr>
</table>

(52) U.S. Cl.
CPC ......... *G02B 6/3598* (2013.01); *G02B 6/3624* (2013.01); *G02B 6/40* (2013.01); *G02B 6/4292* (2013.01); *G01N 2021/399* (2013.01); *G01N 2201/0833* (2013.01); *G02B 6/3672* (2013.01)

(58) Field of Classification Search
CPC .......... G02B 6/04; G02B 6/3624; G02B 6/40; G01J 3/0218; G01J 3/42
See application file for complete search history.

(56) References Cited

U.S. PATENT DOCUMENTS

<table>
<tr><td>4,915,468</td><td>A</td><td>4/1990</td><td>Kim et al.</td></tr>
<tr><td>4,989,979</td><td>A</td><td>2/1991</td><td>Buckman</td></tr>
<tr><td>5,042,905</td><td>A</td><td>8/1991</td><td>Anjan</td></tr>
<tr><td>5,396,506</td><td>A</td><td>3/1995</td><td>Ball</td></tr>
<tr><td>5,448,071</td><td>A</td><td>9/1995</td><td>Mccaul et al.</td></tr>
<tr><td>5,477,323</td><td>A</td><td>12/1995</td><td>Andrews et al.</td></tr>
<tr><td>5,506,721</td><td>A</td><td>4/1996</td><td>Hikami et al.</td></tr>
<tr><td>5,621,213</td><td>A</td><td>4/1997</td><td>Barshad</td></tr>
<tr><td>5,798,840</td><td>A</td><td>8/1998</td><td>Beiting</td></tr>
<tr><td>5,802,222</td><td>A</td><td>9/1998</td><td>Rasch et al.</td></tr>
<tr><td>5,813,767</td><td>A</td><td>9/1998</td><td>Calabro et al.</td></tr>
<tr><td>5,960,129</td><td>A</td><td>9/1999</td><td>Kleinschmitt</td></tr>
<tr><td>6,016,372</td><td>A</td><td>1/2000</td><td>Fein et al.</td></tr>
<tr><td>6,150,661</td><td>A</td><td>11/2000</td><td>Mccaul et al.</td></tr>
<tr><td>6,160,255</td><td>A</td><td>12/2000</td><td>Sausa</td></tr>
<tr><td>6,345,134</td><td>B1</td><td>2/2002</td><td>Laming et al.</td></tr>
<tr><td>6,455,851</td><td>B1</td><td>9/2002</td><td>Lord et al.</td></tr>
<tr><td>6,519,385</td><td>B1</td><td>2/2003</td><td>Green</td></tr>
<tr><td>6,593,573</td><td>B1</td><td>7/2003</td><td>Mccann et al.</td></tr>
<tr><td>6,766,070</td><td>B2</td><td>7/2004</td><td>Williams et al.</td></tr>
<tr><td>6,791,689</td><td>B1</td><td>9/2004</td><td>Weckström</td></tr>
<tr><td>7,248,755</td><td>B2</td><td>7/2007</td><td>Sappy et al.</td></tr>
<tr><td>7,342,947</td><td>B1</td><td>3/2008</td><td>Minden</td></tr>
<tr><td>2001/0012429</td><td>A1</td><td>8/2001</td><td>Wach</td></tr>
<tr><td>2003/0107739</td><td>A1</td><td>6/2003</td><td>Lehmann</td></tr>
<tr><td>2008/0285916</td><td>A1*</td><td>11/2008</td><td>Sappey ................ G01J 3/1895 385/27</td></tr>
<tr><td>2010/0265493</td><td>A1</td><td>10/2010</td><td>Jiang</td></tr>
<tr><td>2011/0122396</td><td>A1*</td><td>5/2011</td><td>Ivaldi ................ G01N 21/3103 356/51</td></tr>
<tr><td>2014/0011266</td><td>A1*</td><td>1/2014</td><td>Webster .................... B01L 7/52 435/286.1</td></tr>
</table>

FOREIGN PATENT DOCUMENTS

<table>
<tr><td>CN</td><td>102654455 A</td><td>9/2012</td></tr>
<tr><td>CN</td><td>103604773 A</td><td>2/2014</td></tr>
<tr><td>EP</td><td>0766080 A1</td><td>4/1997</td></tr>
</table>

OTHER PUBLICATIONS

Allen et al. (2002) "Tunable Diode Laser Sensing and Combustion Control" Applied Combustion Diagnostics, chapter 18.

Baer et al. (1994) "Multiplexed Diode-Laser Sensor System for Simultaneous H20, 02, and Temperature Measurements" Optics Letters 19(22):1900-1902.

Docquier and Candel (2002) "Combustion control and sensors: a review" Progress in Energy and Combustion Science 28, 107-150.

Ebert et al. (1998) "Simultaneous Laser-Based in situ Detection of Oxygen and Water in a Waste Incinerator for Active Combustion Control Purposes" 27th Symposium on Combustion pp. 1301-1308.

Ebert et al. (2000) "Simultaneous Diode-Laser-Based in Situ Detection of Multiple Species and Temperature in a Gas-Fired Power Plant" Proceedings of the Combustion Institute 28:423.

Ebert et al. (2000) "The Use of Lasers as the Basis for Combustion Equipment Control" at TOTem, Intelligent Combustion Control pp. 1-15.

Furlong et al. (1998) "Diode Laser Sensors for Real-Time Control of Pulsed Combustion Systems": AIAA/SAE/ASME/ASEE Joint Propulsion Conference and Exhibit, pp. 1-8, 1, XP001148178.

Furlong et al. (1998) "Real-Time Adaptive Combustion Control Using Diode-Laser Absorption Sensors," 27th Symposium on Combustion pp. 103-111.

International Search Report from PCT/US2015/061387 dated Feb. 4, 2016.

Liu et al. (2003) "Diode Laser Absorption Diagnostics for Measurements in Practical Combustion Flow Fields" 39th AIAA/ASME/SAE/ASEE Joint Propulsion Conference and Exhibit, Paper No. AIAA-2003-4581 pp. 1-6.

Miller et al. (1996) "Diode laser-based air mass flux sensor for subsonic aeropropulsion inlets" Applied Optics 35:4905.

Ouyang et al. (1992) "Tomographic Absorption Spectroscopy of Combustion Gases using Tunable Infrared Diode Lasers," Paper No. 1637-20, SPIE Conference on Environmental and Process Monitoring Technologies, pp. 163-172.

Phillippe et al. (1993) "Laser diode wavelength-modulation spectroscopy for simultaneous measurement of temperature, pressure, and velocity in shock-heated oxygen flows" Applied Optics 32:6090.

Sanders et al. (2000) "Diode-Laser Sensor for Monitoring Multiple Combustion Parameters in Pulse Detonation Engines" Proceedings of the Combustion Institute 28:587.

Sanders et al. (2001) "Diode-laser absorption sensor for line-of-sight gas temperature distributions" Applied Optics 40:4404.

Teichert et al. (2003) "Simultaneous in situ measurement of CO H2O, and gas temperatures in a full-sized coal-fired power plant by near-infrared diode lasers" Applied Optics 42:2043.

Upschulte et al. (1999) "Measurements of CO, CO2, OH, and H2O in room-temperature and combustion gases by use of a broadly current-tuned multisection InGaAsP diode laser" Applied Optics 38:1506.

Varghese et al. (1997) "Temperature and CO2 Concentration Profiles in Flames Measured by Laster Absorption Tomography," Paper 97-0317, AIAA 35th Aerospace Sciences Meeting, Reno, NV.

Villarreal and Varghese (2005) Applied Optics 44:6786-6795, Frequency-resolved absorption tomography with tunable diode lasers.

Webber et al. (2000) "In Situ Combustion Measurements of CO, CO2, H2O and Temperature Using Diode Laser Absorption Sensors" Proceedings of the Combustion Institute 28:407.

Wolfrum (1998) "Lasers in Combustion: From Basic Theory to Practical Devices" 27th Symposium on Combustion pp. 1-41.

Extended European Search Report received for corresponding Application No. EP15873925.0, dated Jul. 26, 2018, 8 pages.

* cited by examiner

TDLAS ARCHITECTURE FOR WIDELY SPACED WAVELENGTHS

RELATED APPLICATIONS

This application is a 35 U.S.C. § 371 national phase application of PCT/US2015/061387 (WO 2016/105704), filed on Nov. 18, 2015, entitled "TDLAS Architecture for Widely Spaced Wavelengths", which application claims the benefit of U.S. Provisional Application Ser. No. 62/096,426, filed Dec. 23, 2014, which is incorporated herein by reference in its entirety.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND

Tunable diode laser absorption spectroscopy (TDLAS) is a well-proven technique for detecting and measuring the concentrations of various species in a gaseous mixture. TDLAS relies on the unique absorption spectrum of the species being targeted to measure an attenuation of a diode laser beam at a very specific wavelength, tuned over an absorption line of the species being measured, as it passes through a measurement region. At wavelengths even slightly different from these absorption lines, there is essentially no absorption.

Generally, in operation the wavelength of the diode laser beam is scanned over a small range that encompasses at least one absorption line of the species of interest, as well as a region in which there is no absorption. The light intensities of the light transmitted through the sample are measured by a photodetector. The photodetector signals are then analyzed to obtain an average concentration of the target species over the length of the beam path with knowledge of the temperature.

Because the molecules of each target species absorb light at a particular frequency, a different diode laser is generally required to measure different species. For certain applications, TDLAS systems need to use wavelengths encompassing a wide wavelength range from approximately 760 nm for oxygen ($O_2$) detection to 2.33 microns for carbon monoxide (CO) detection. Wavelength-multiplexed TDLAS systems exist that use wavelengths from 760 nm to 1559 nm with the 1559 nm wavelength used for CO detection. However, some applications require a lower detection limit for CO than can be achieved at 1559 nm. For instance, in coal-fired boiler applications, the measurement path length can be over 10 meters and in the combustion zone the CO concentration can range upward from 5000 ppm. Under these conditions, CO detection using the second overtone band in the 1550 nm region works adequately. Because this wavelength region is widely used in telecommunications, single-mode optical fiber with high transmission is readily available, along with robust fiber-optic components such as switches, lasers and splitters.

However, certain applications require detection capability for CO at much lower concentrations and over a much shorter path. For example, detection of CO in the range of 100 ppm over a 1 meter path involves measuring roughly a 500 times smaller effect on the light intensity of the transmitted beam, making detection substantially more difficult than in the coal boiler application. This necessitates measuring CO on the first overtone at about 2.33 microns at which CO has a transition line strength that is approximately 500 times higher than that at 1559 nm.

Recently, TDLAS systems have been deployed that operate at wavelengths from 1350 nm to 2 microns. The extension to 2 microns allows sensitive detection of $CO_2$ for carbon balance determination in steel applications. In many steel applications, $O_2$ need not be measured so the 760 nm wavelength is not required. In spite of this wavelength range extension, the same single-mode fiber can be used to transmit, in single-mode fashion, light in this entire wavelength range (1350 nm-2000 nm). However, further extension to about 2.33 microns for sensitive CO detection, and a requirement to measure $O_2$ at 760 nm necessitates a completely different architecture due to the inability of a single type of single-mode fiber to deliver wavelengths from about 760 nm to 2.33 microns single mode with high transmission and low bend loss.

Since light at wavelengths from about 760 nm-2.33 microns cannot co-propagate on the same single-mode fiber, a new wavelength multiplexing scheme must be devised for applications requiring both $O_2$ detection and sensitive CO detection. One such application is glass furnace monitoring. Three wavelengths are required to measure $O_2$, water ($H_2O$), and CO for this application with CO detection required at the 100 ppm level or lower. Also required for this application is the ability to measure across approximately 10 paths simultaneously, or nearly simultaneously.

SUMMARY

According to various sets of embodiments, a system, apparatus, and method for TDLAS for widely spaced wavelengths is provided.

In an aspect, a system for widely spaced wavelength tunable diode laser absorption spectroscopy includes at least a first and second tunable diode laser. The first tunable diode laser may generate laser light at a first wavelength, and the second tunable diode laser may generate laser light at a second wavelength. Laser light of the first and second wavelengths are utilized that cannot co-propagate in a single transverse mode with simultaneously high efficiency on a single-mode fiber.

The system includes a first fiber having a proximal end and a distal end, the first fiber being optically coupled to the first tunable diode laser at the proximal end, the first fiber being a single mode optical fiber configured to carry light in the first wavelength. A second fiber is provided having a proximal end and a distal end, the second fiber being optically coupled to the second tunable diode laser at the proximal end, the second fiber being a single mode optical fiber configured to carry light in the second wavelength. A fiber bundle is provided, comprising the distal ends of at least the first and second fibers, wherein the distal ends of the first and second fibers are stripped of their respective coatings, and wherein a first fiber optic core of the first fiber and a second fiber optic core of the second fiber are arranged with their claddings adjacent to each other forming a bundled configuration.

The system further includes one or more pitch heads comprising a transmitting optic, the transmitting optic optically coupled to the first and second tunable diode lasers via the distal ends of the first and second fibers of the fiber bundle. The pitch head is configured to project respective beams of laser light from the first fiber optic core and the second fiber optic core, wherein the pitch head is oriented to project the respective beams from each of the first and second fiber optic cores through a measurement zone. One or more sensors are provided, each sensor comprising respectively at least one photodetector, each of the at least one photodetector being configured to detect an optical power of light in the first and second wavelengths. Furthermore, one or more catch heads are located across the measurement zone by a select distance from the one or more pitch head, the one or more catch head in optical communication with a respective pitch head of the one or more pitch head to receive the respective beams of the first and second fiber optic cores and direct the respective beams onto at least one of the one or more sensor.

In another aspect, a pitch head may be utilized for widely spaced wavelength tunable diode laser absorption spectroscopy. The pitch head includes a housing configured to optically couple with a fiber bundle, the fiber bundle comprising distal ends of at least a first and second input fibers, wherein the first input fiber is a single mode fiber that carries laser light at a first wavelength and the second input fiber is a single-mode fiber that carries laser light at a second wavelength, wherein laser light of the first and second wavelengths cannot co-propagate on a single-mode fiber. The distal ends of at least the first and second input fibers are stripped of their respective coatings, and wherein a first fiber optic core of the first input fiber, and a second fiber optic core of the second input fiber are arranged with their claddings adjacent to each other forming a bundled configuration.

The pitch head may further include a pitch optic configured to project respective beams of laser light from each of the at least first and second fiber optic cores, through a measurement zone. The housing is oriented such that the respective beams reach a catch head located across the measurement zone a select distance from the housing.

In yet another aspect, a method for widely spaced wavelength tunable laser diode laser spectroscopy is provided. The method includes generating a first laser beam of a first wavelength, generating a second laser beam of a second wavelength, carrying the first laser beam on a first single-mode optical fiber and the second laser beam on a second single-mode optical fiber, wherein laser light of the first and second wavelengths cannot co-propagate on a single-mode fiber, stripping distal ends of the first and second single-mode optical fiber of their respective coatings, arranging a first fiber optic core of the first single-mode optical fiber with its cladding adjacent to the cladding of a second fiber optic core of the second single-mode optical fiber forming a bundled configuration, and forming a fiber bundle from the bundled configuration of the first and second fiber optic cores. The method further includes transmitting, with a pitch head, respective beams of laser light, from each of the first and second fiber optic cores of the fiber bundle, through a measurement zone, receiving each respective beam at a catch head located across the measurement zone a select distance from the pitch head, and detecting, at the catch head, an optical power of light in each of the first and second wavelengths, and determining a concentration of targeted species having an absorption line at the first and second wavelengths.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/of" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise. As is well known in the art, the same device may typically be used for either multiplexing or demultiplexing, depending upon the direction of the light which passes through it. Consequently, the term "multiplexer" or "mux" as used herein will be understood to include both multiplexing and demultiplexing functions.

Conventional wavelength division multiplexing (WDM) techniques cannot be used to multiplex signals having wavelengths that span the range of 760 nm-2330 nm into a single-mode fiber, as it would be extremely difficult to create or find a suitable output fiber to carry multiple signals spanning the range of wavelengths.

Fiber Bundle TDLAS Architecture

Figure 1:
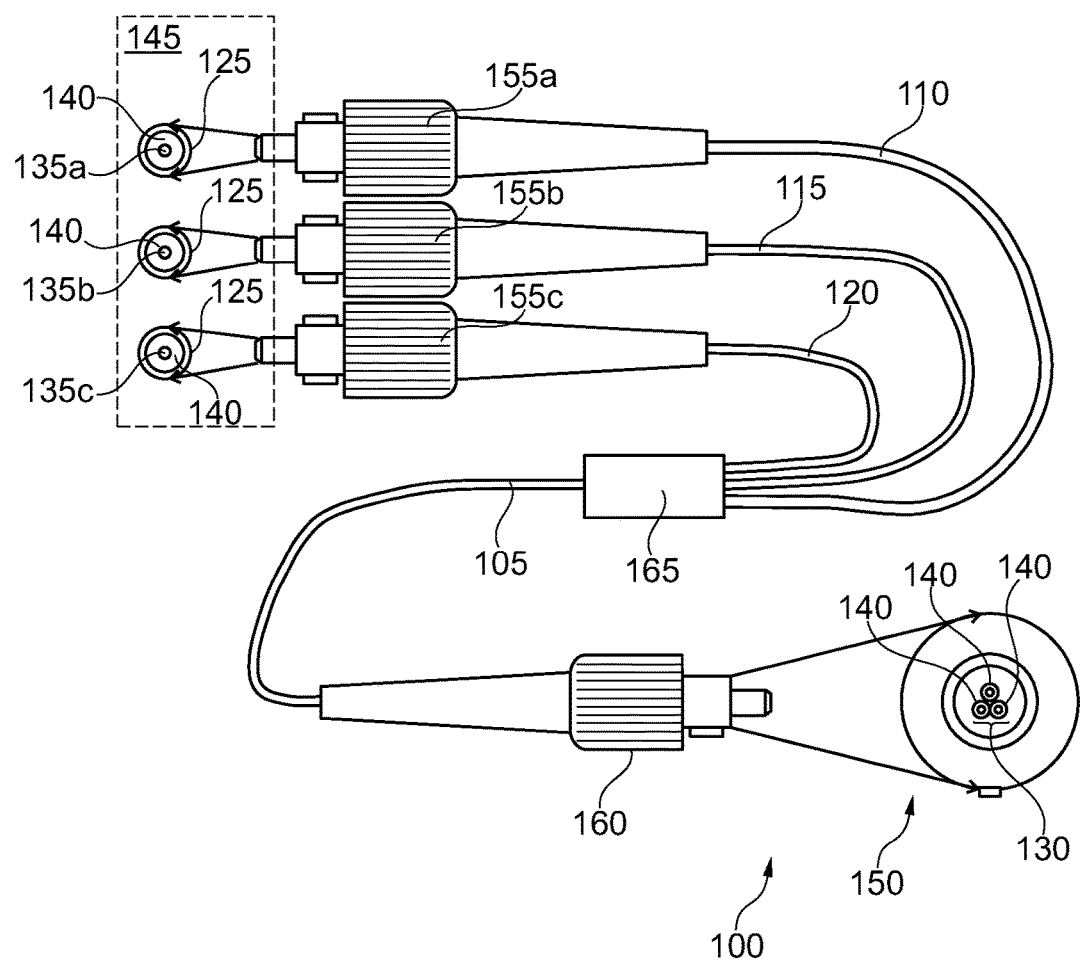
FIG. 1 illustrates a fiber bundle assembly for pitch heads in a widely spaced wavelength TDLAS system.

FIG. 1 illustrates a fiber bundle assembly 100 capable of transmitting beams at wavelengths spanning the 760 nm-2330 nm range, in single mode operation, from a single transmitting (pitch) head, and to a corresponding single receiving (catch) head. The fiber bundle assembly 100 includes a fiber bundle 105 comprising the cores 135a, 135b, 135c (135 collectively) of three single-mode optical fibers 110, 115, 120. Each of the single-mode optical fibers 110, 115, 120 has a distal and proximal end. The single-mode optical fibers 110, 115, 120 are optically coupled at their proximal ends to a respective tunable diode laser. Each respective tunable diode laser may be tuned to generate laser light at a selected wavelength. These wavelengths may be chosen to correspond with the absorption lines of one or more target species.

Each wavelength of laser beam is carried by a respective single-mode fiber 110, 115, 120 appropriate for that wavelength. For example, according to one set of embodiments, the single-mode fiber 110 carries 2330 nm wavelength light, single-mode fiber 115 carries 1350 nm light, and single-mode fiber 120 carries 760 nm light. In further embodiments, SM1950 optical fiber may be used for single-mode fiber 110 to carry 2330 nm light, SMF28e optical fiber may be used for single-mode fiber 115 to carry 1350 nm light, and SM750 optical fiber may be used for single-mode optical fiber 120 to carry 760 nm light. In embodiments utilizing SM1950 optical fiber, light at 2330 nm experiences loss at 1 dB/m. However, this level of loss may be acceptable over short lengths.

The three single-mode fibers 110, 115, 120 are combined, at coupling joint 165, to form fiber bundle 105. According to one set of embodiments, the distal ends of each of the single-mode optical fibers 110, 115, 120 are stripped of their coating 125. In various embodiments, the coating 125 removed may include, without limitation, some or all of the jacketing or buffer material of the optical fiber, but is not intended to include the cladding immediately adjacent to the core. The stripped optical fibers 110, 115, 120 are then arranged in a triangular configuration 130 and bundled to form fiber bundle 105 with their respective claddings abutting. In some embodiments, coupling joint 165 may provide a protective structure around the point at which the three stripped optical fibers 110, 115, 120 meet to form the fiber bundle 105. The coupling joint 165 may further stabilize or keep the optical fibers 110, 115, 120 in place relative to the fiber bundle 105. In some embodiments, cores 135 are bundled in a triangular configuration 130 in which the cores 135 are spaced apart by 125 microns—the thickness of the cladding 140 between two adjacent optical fibers 110, 115, 120. In an alternative set of embodiments, a multi-core fiber may be substituted for the bundled fibers. In various embodiments, the fiber bundle 105 may further comprise a jacket, buffer, or other encasing applied to the bundled configuration of the fiber optic cores 135 for further physical protection of the exposed cores, to maintain the triangular configuration of the cores, and to improve signal characteristics. An achromatic doublet (not shown), or other suitable optical collimator, can be used to collimate the light from the fiber bundle 105. However, due to the lateral offset of the light in the focal plane, the beams diverge after exiting the collimator by about 2 milliradians (125 microns/50 mm f.l.). Thus, each of the different wavelengths of laser beams will arrive at a catch side at a different location, depending on the path length. This is illustrated and described in more detail below with respect to FIG. 6.

Thus, the fiber bundle assembly 100 may require a system to maintain alignment between the pitch and catch side optics. An example of such an alignment system is described in U.S. Pat. No. 7,248,755 ('755 patent), entitled "Method and Apparatus for the Monitoring and Control of Combustion," which is incorporated herein by reference in its entirety. The auto-alignment system described in the '755 patent overcomes such misalignment issues by automatically and dynamically adjusting the tip and tilt of either the pitch side optical head or the catch side optical head, or both pitch and catch side optical heads, to maintain alignment and ensure an adequate signal is received at each frequency. The auto-alignment system is described in more detail below with respect to FIG. 6.

In some embodiments, each wavelength laser beam may require realignment of the pitch and/or catch optics by the auto-alignment system. In such embodiments, time-division multiplexing (TDM) may be appropriate. By adopting TDM instead of a WDM based system, the need to perform wavelength demultiplexing in the catch head can be avoided. A conventional wavelength demultiplexer requires the use of additional optical fiber in the catch head. However, at a wavelength of 2330 nm, additional optical fiber can highly attenuate the received signal.

Each of the input connectors 155a, 155b, 155c (155 collectively) are coupled to a respective light source (not shown). For example, in various embodiments, input connector 155a may couple single-mode optical fiber 110 to a 2330 nm wavelength light source, input connector 155b may couple single-mode optical fiber 215 to a 1350 nm wavelength light source, and input connector 155c may couple single-mode optical fiber 220 to a 760 nm wavelength light source. The fiber bundle 105 is then coupled by an output connector 160 to the pitch head or a transmitting optic.

In operation, each of the light sources may be turned on and off in an alternating fashion following a TDM scheme so that only one light source is transmitted at a given time. For example, in various embodiments, a first light source generating light at about 2330 nm may be turned on. The 2330 nm signal is carried by single-mode optical fiber 110, and as part of fiber bundle 105 on the respective core 135 corresponding to optical fiber 110, to a transmitting optic. The first light source is then turned off, and a second light source generating light at 1350 nm is turned on. The 1350 nm signal is then carried by single-mode optical fiber 115, and as part of fiber bundle 105 on the respective core 135 corresponding to optical fiber 115, to a transmitting optic. The second light source is then turned off, and a third light source generating light at 760 nm is turned on. The 760 nm signal is then carried by single-mode optical fiber 120, and as part of fiber bundle 105 on the respective core 135 corresponding to optical fiber 120, to a transmitting optic. Alternatively a 1×2 optical switch can be used to switch the light from each of the laser sources into the appropriate leg of the single mode fiber bundle or to a dummy optical path, so that light at only a single wavelength is present at the distal end of the fiber bundle at a time. The switched embodiment allows for more stable operation of the diode lasers.

Using optical fiber to catch and transmit the light back to a centrally located rack for detection and quantification becomes problematic when using the long wavelength of about 2330 nm for CO detection, as this wavelength suffers high attenuation in silica fibers (~1 dB/m). For example, arrangements may have a system deployed at a refinery where catch heads may be mounted on different furnaces that can, in many instances, be separated by a distance of 1 kilometer or more. This requires too much fiber to be able to detect the transmitted light at 2330 nm, with transmission loss on the order of $\sim 1\times 10^{-100}$ for 1 kilometer of fiber. The other issue with long runs of multimode catch fiber is that mode noise generated by interference effects in the fiber creates transmission noise that impedes detection, fitting, and quantification of absorption peaks.

Figure 2:
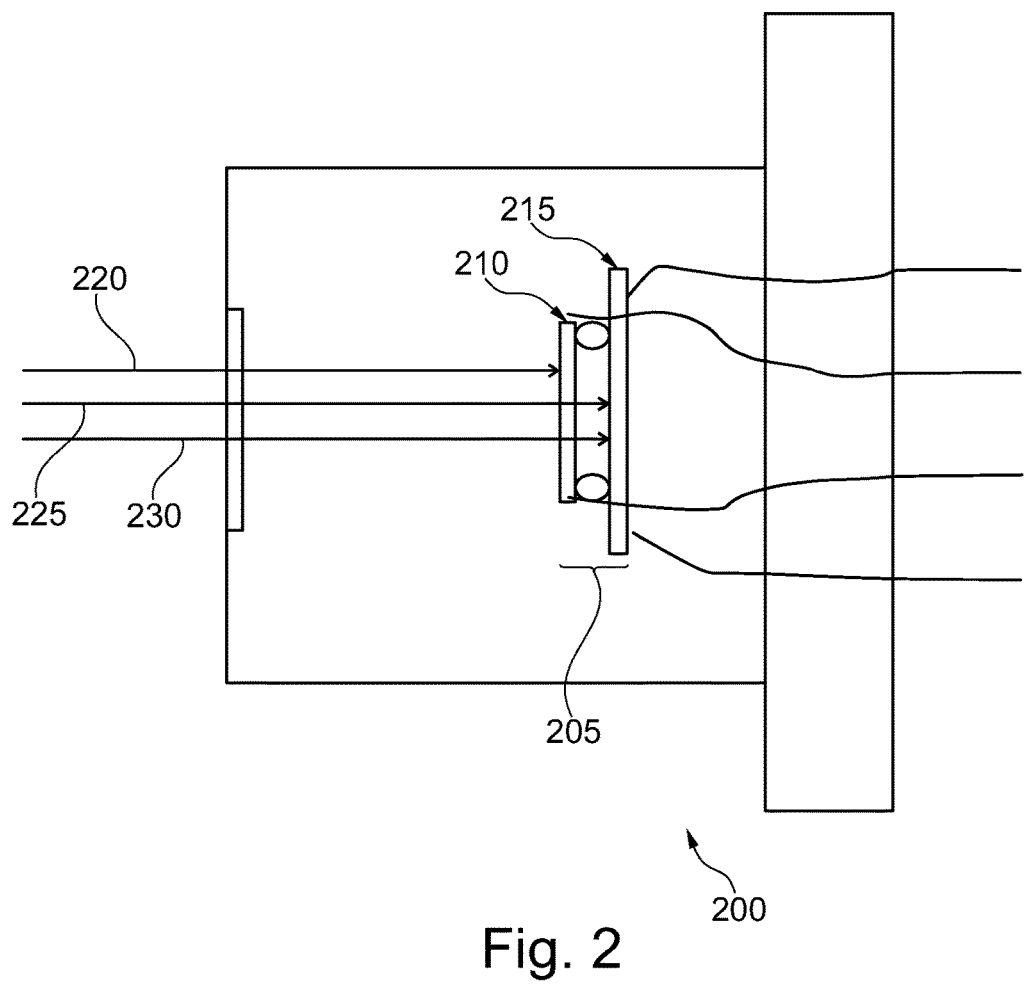
FIG. 2 illustrates a dual band photodetector for use in a widely spaced wavelength TDLAS system.

FIG. 2 illustrates a cross-sectional schematic view of a dual band detector 200 that may be used within, or in close proximity to, the catch heads in combination with a time-division multiplexing strategy to detect each of a first received signal 220, second received signal 225, and third received signal 230 at each wavelength respectively associated with the received signals 220, 225, 230, without having to use a wavelength demultiplexer. Thus, dual band detector 200 addresses the potential attenuation of 2330 nm wavelength light carried over long lengths of fiber by allowing detection, digitization, and/or signal processing to occur in the catch head. The resulting data can be transmitted back to a central rack for final processing and quantification via Ethernet protocol on either copper or optical fiber media.

The dual band detector 200 comprises a sandwiched detector assembly 305 with a first photodetector layer 210 and a second photodetector layer 215. Each of the first and second photodetector layers 210, 215 are configured so that each of the respective wavelengths of each received signal 220, 225, 230 can be detected. For example, in some embodiments, the first photodetector layer 210 may be a silicon (Si) PIN photodetector layer and the second photodetector layer 215 may be an extended indium gallium arsenide (ex-InGaAs) photodetector for detecting the first received signal 220 having a wavelength of 760 nm, a second received signal 225 having a wavelength of 1350 nm, and a third received signal 230 having a wavelength of 2330 nm. The 760 nm light from the first received signal is detected well by the Si PIN photodetector 210, however wavelengths in the near-infrared (~1-3 microns), including the wavelengths of the second and third received signals 225, 330, pass through the Si PIN photodetector 210 undetected. Thus, the longer wavelengths impinge on the second photodetector layer, the ex-InGaAs photodetector 215, which is sensitive from about 1.3 microns to 2.5 microns. However, the ex-InGaAs photodetector 215 cannot distinguish between the second received signal 225 and the third received signal 230 without recourse to more complicated techniques such as frequency division multiplexing (FDM), i.e. modulating the second and third received signal at two different frequencies and discriminating based on the frequency of the detected light. Thus, without FDM, the dual band detector 200 cannot be used for detecting the signals simultaneously. By utilizing TDM, as suggested above for use with fiber bundle assembly 100, only one of the three received signals 220, 225, 230 will be turned on at any given time, eliminating the need to physically separate the 1350 nm and 2330 nm beams of the second 225 and third 230 received signals. In this manner, the use of TDM and the dual band detector can eliminate the need for demultiplexing at the receiving side.

Figure 3:
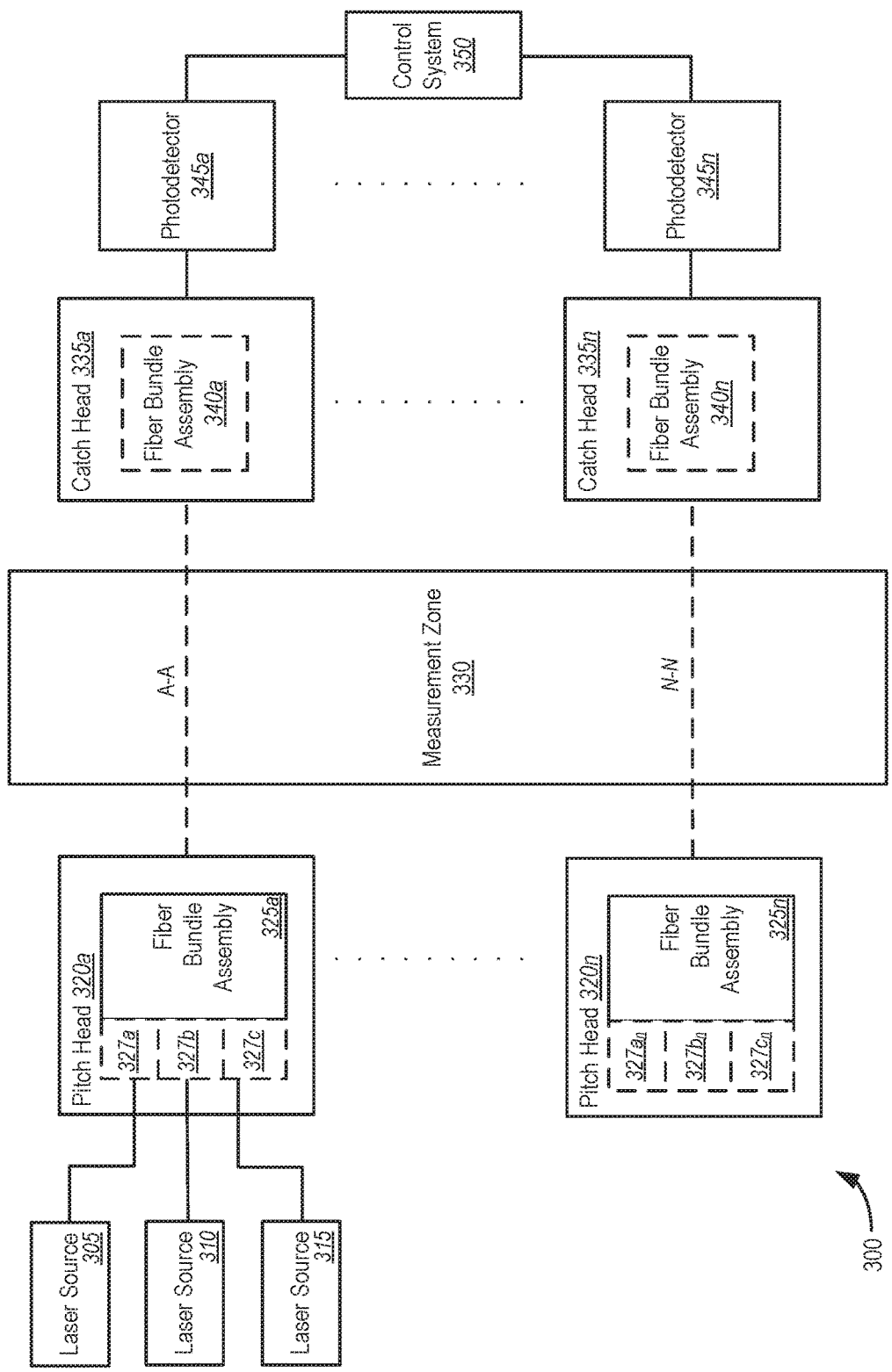
FIG. 3 illustrates a system block diagram for a widely spaced wavelength TDLAS system.

FIG. 3 is a block diagram of a widely spaced wavelength TDLAS system 300, according to various embodiments. The widely spaced wavelength TDLAS system 300 comprises a first laser source 305, second laser source 310, and third laser source 315 for generating laser light at a particular wavelength. For example, laser sources 305, 310, 315 may be a series of tunable diode lasers. Each of the first, second, and third laser sources 305, 310, 315 are configured to generate a laser beam of a specific wavelength that corresponds to an absorption line in an absorption spectrum for each species of interest in the measurement zone. For example, in some embodiments, the first laser source 305 generates a laser beam at 760 nm corresponding to the detection of oxygen molecules ($O_2$), the second laser source 310 generates a laser beam at 1350 nm corresponding to the detection of water molecules ($H_2O$), and the third laser source 315 generates a laser beam at 2330 nm corresponding to the detection of carbon monoxide (CO) molecules. In this example, only three laser sources are provided by way of illustration, and it is to be understood that in other embodiments, any number of laser sources may be used to generate laser beams at any other number of selected absorption line wavelengths. In some embodiments, each of the laser sources 305, 310, 315 are centrally housed and controlled in a rack or cabinet that may be located remotely away from a measurement site.

The signals from each of the laser sources 305, 310, 315 are optically coupled to a plurality of pitch heads 320a-320n. In some embodiments, the signals from each of the laser sources 305, 310, 315 are switched between each of the plurality of pitch heads 320a-320n to make measurements along each of the multiple paths A-A through N-N. To ensure single-mode behavior, an optical switch 327 may be provided for each wavelength of light to each pitch head 320a-320n, to allow one wavelength to be transmitted, in a serial manner, from each pitch head.

Alternatively, some embodiments call for the signals from each of the laser sources 305, 310, 315 to be split along each of the multiple paths so as to provide the respective laser beams to each of the plurality of pitch heads 320a-320n in parallel (simultaneously). Widely spaced wavelength TDLAS systems are often used in measurement zones that are essentially particle free, such as glass furnaces and other natural gas fired furnaces, resulting in negligible laser power attenuation caused by the furnaces themselves. Thus, the light from the laser sources 305, 310, 315 can be split to service the multiple paths in parallel rather than switching the light serially between each pitch head 320a-320n, which is required for high scattering applications like coal and steel electric arc furnaces where laser power attenuation is sufficiently high that all power must be available to measure on every path. In combination with a time multiplexing strategy described above, all paths A-A through N-N can be measured simultaneously for a species, and switching can occur between the measured species (i.e. wavelength) rather than between the multiple paths.

Fiber bundle assemblies 325a-325n are provided for delivering each of the laser beams from each of the laser sources 305, 310, 315 to a corresponding pitch head 320a-320n. In one set of embodiments, the signals from each of the laser sources 305, 310, 315 are carried over a respective single-mode fiber corresponding to the wavelength of each signal, as described with respect to FIGS. 1 & 2 above. The fiber bundle assemblies 325a-325n then transmit each of the laser beams to produce a discrete time division multiplexed signal having only one wavelength beam at a given time. Single mode operation is maintained over the entire range of wavelengths and delivered to a single set of pitch optics in the pitch heads 320a-320n.

The pitch heads 320a-320n may include a collimator or other pitch optics to project the discrete time division multiplexed beams across measurement zone 330. Each respective catch head 335a-335n is spaced, across the measurement zone 330, from a corresponding pitch head 335a-335n. Each of the pitch heads 320a-320n is aligned with a respective catch head 335a-335n such that each discrete time division multiplexed beam is received by the catch head. In some embodiments, the pitch and/or catch heads are aligned via an auto-alignment system as described in the '755 patent, and in further detail with respect to FIG. 6 below.

In various embodiments, catch heads 335a-335n may also optionally comprise respective fiber bundle assemblies 340a-340n for receiving each of the time-division multiplexed beams. For example, in some embodiments, a fiber bundle assembly 335a-335n may be used such that a core corresponding to the particular wavelength of the transmitted signal is aligned to receive the beam. For example, in some embodiments, the catch head 335a may include a lens that focuses the wavelength-bundled beam onto the appropriate fiber of the fiber bundle. The auto-alignment system may then adjust the lens, catch side fiber bundle assembly 340a, pitch side fiber bundle assembly, pitch head, or a combination of these elements to align the beam to the catch side fiber bundle assembly 340a.

The received beam is directed by the catch head 335a-335n onto a respective photodetector 345a-345n. In some embodiments, a corresponding single-mode fiber is used to carry each wavelength of the signal. In other embodiments, the signal may be received, and carried by, a multi-mode fiber. In various embodiments, the photodetector 345a-345n may be in close proximity to the catch head 335a-335n so as to minimize the lengths of optical fiber used to carry the signal from the catch head 335a-335n to the photodetector 345a-345n. In some further embodiments, a photodetector 345a-345n may be provided within each catch head 335a-335n, such that receiving optic(s) in each catch head 335a-335n focuses the received beam directly onto the respective photodetector 345a-345n.

Each photodetector 345a-345n is configured to detect and measure the light intensities of each wavelength of light received. In one embodiment, the photodetectors 345a-345n are dual band photodetectors 200 as described in FIG. 2. The measurements from the photodetectors 345a-345n are then transmitted back to a control system 350 for further processing and analysis. In some embodiments, the control system 350 may be located on a central rack and data may be transmitted back to the central rack directly over a physical link such as copper or optical fiber media, or through communications network that includes without limitation a local area network (LAN), a wide area network (WAN), a virtual network, the internet, an intranet, or a personal area network. Connection to the communications network may be either wired or wireless. In various embodiments, the control system 350 may be used as part of a feedback loop to control the combustion environment in the measurement zone 330. In some embodiments, some processing (e.g. waveform averaging) of the received signal may occur in the heads by, for example, a field programmable gate array ("FPGA") to minimize the bandwidth transmission requirements back to the control system.

Figure 4:
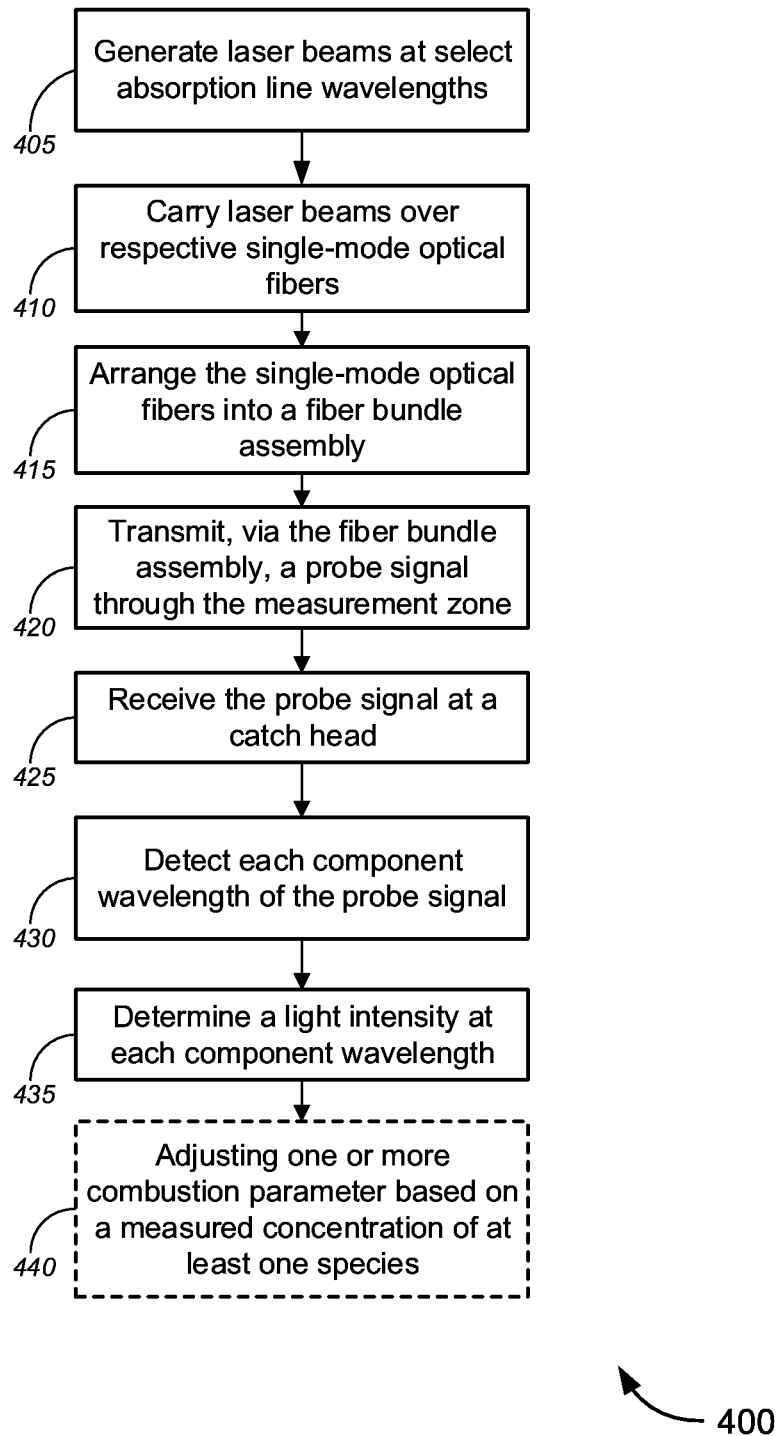
FIG. 4 is a flow chart for a method of utilizing widely spaced wavelength TDLAS.

FIG. 4 is a flow chart of a method for widely spaced wavelength TDLAS 400 according to various embodiments. At block 405, laser beams are selected at select absorption line wavelengths of targeted species. In some embodiments, the laser beams may be generated following a TDM scheme that switches between each laser beam to be generated, as described in further detail below with respect to block 420, while in other embodiments, the laser beams may be generated simultaneously. In one embodiment, laser beams are generated at at least a first wavelength, such as one corresponding to the detection of CO at levels of 100 ppm, and a second wavelength, such as one corresponding to the detection of $O_2$. In this example, the first and second wavelengths may also be so widely spaced such that they cannot be carried by a common single-mode fiber.

Instead, at block 410, each of the laser beams are carried over a respective single-mode optical fiber for each particular wavelength of laser beam. The beams are carried by the respective single-mode optical fibers to a fiber bundle assembly. For example, in some embodiments, a pitch head may comprise all or part of the fiber bundle assembly. In other embodiments, the fiber bundle assembly may be separate from the pitch head.

At block 415, the optical fibers are arranged into a fiber bundle assembly. As described with respect to FIG. 1, above, in various embodiments, the distal ends of each of the optical fibers are stripped of their coatings, and, with their claddings and cores intact, arranged into a triangular configuration. This triangular configuration is packaged to form the fiber bundle.

At block 420, the fiber bundle assembly transmits a probe signal through a measurement zone. The probe signal may comprise component signals at each of the selected wavelengths respectively, with each component signal carried over the corresponding single-mode optical fibers. In various embodiments, only one wavelength of component signal may be transmitted via the fiber bundle assembly at a given time, following a TDM sequence.

At block 425, the probe signal is received at a catch head, spaced across the measurement zone, from the pitch head. In various embodiments, the catch head may use one or more receiving optics to direct the probe signal to a multimode fiber, respective single mode fiber, fiber bundle assembly, photodetector, or otherwise as appropriate for the specific configuration of the catch head. For example, in some embodiments, the catch head may employ a corresponding fiber bundle assembly that can be used to receive each wavelength of component signal with a single-mode optical fiber corresponding to that wavelength. In further embodiments, the catch head may also employ an auto-alignment system, as described in the '755 patent, which dynamically adjusts the catch head tilt and tip in order to maintain alignment with the pitch head based on detected light intensities of the received wavelength-bundled beam. In some embodiments, a photodetector may be provided within the catch head, and the catch head may direct the received wavelength-bundled beam through free space (air) directly to the internal photodetector.

At block 430, each component wavelength of the probe signal is detected. To accomplish this, a single photodetector assembly may be provided that is capable of detecting each component wavelength, such as by using a TDM system in combination with the dual band photodetector 200 described with respect to FIG. 2. Alternatively, a separate photodetector may be used that is sensitive to each selected wavelength respectively.

At block 435, a light intensity is determined for each respective component wavelength via the photodetector. The light intensity can then be further processed by other components, located in the catch head or separately at a remote site, to determine a relative concentration of a targeted species in the measurement zone, over the path of the probe signal.

At optional block 440, one or more combustion parameter is adjusted based on a measured concentration of at least one species in the measurement zone. Combustion parameters may include, without limitation, a fuel composition, concentration, quantity, air to fuel ratio, or other fuel related parameter; air intake or valve parameters; overall furnace temperature; voltage supplied to an electrode in an electric arc furnace; or any other input parameter affecting the combustion properties within the measurement zone.

In one set of embodiments, a control system may adjust one or more combustion parameters based on the determination of the concentration of various targeted species. In some embodiments, the targeted species may be indicative of various characteristics of the combustion process, such as combustion balance, efficiency, and emissions generated by the combustion process. For example, the air to fuel ratio may be adjusted corresponding to the measured concentration of CO and $O_2$; a fuel concentration may be adjusted corresponding to the measured concentration of CO, $CO_2$, $O_2$, or combination of CO, $CO_2$, and $O_2$; and so on. A combustion parameter may be adjusted based on a corresponding measured concentration of at least one species.

In further embodiments, the combustion parameters may be adjusted independently in each area of the measurement zone based on measurements corresponding to the respective areas of the measurement zone. For example, a measured concentration derived from the measurements of two or more pairs of pitch and catch heads may correspond to an area of the measurement zone defined by the respective measurement path of each pair of pitch and catch heads. Thus, based on the measured concentrations in the above defined area, combustion parameters may be adjusted locally in the defined area. For example, one or more burners in a conventional furnace that most directly affect the defined area may be identified and the combustion parameters may be adjusted for the identified burners independently.

Figure 5:
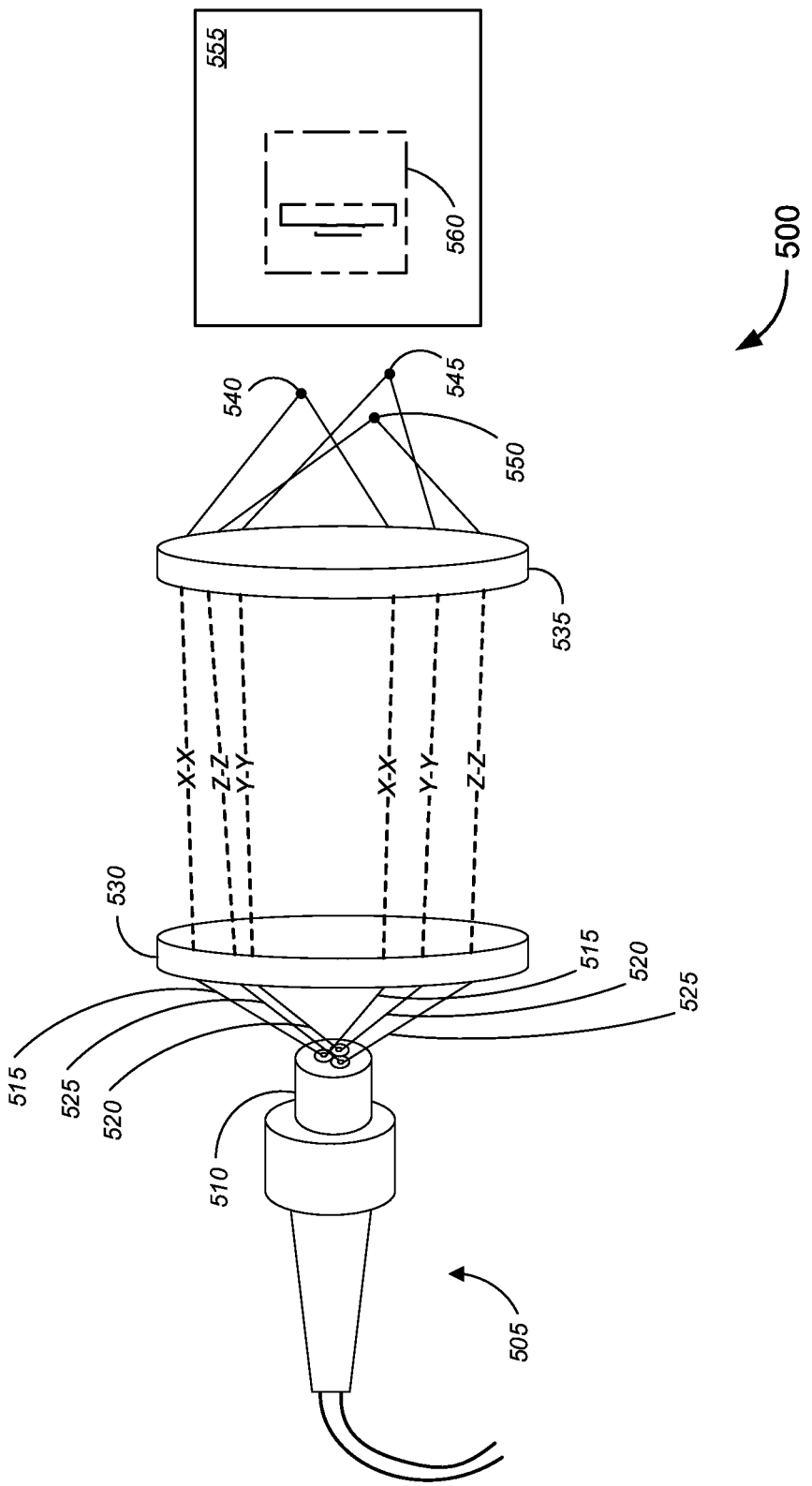
FIG. 5 illustrates beam divergence from a fiber bundle assembly in a widely spaced TDLAS system.

FIG. 5 schematically depicts the beam divergence from the various cores of a fiber bundle assembly in widely spaced wavelength TDLAS system 500. The widely spaced wavelength TDLAS system 500 includes a pitch side fiber bundle assembly 505 positioned behind a transmit collimating optic 530, receive lens 535, and catch head 555. The catch head may optionally include a photodetector 560, depicted in phantom lines. As described above with respect to FIG. 1, each pitch side fiber bundle assembly 505 includes a fiber bundle having three single-mode optical fibers. Each single-mode optical fiber carries a respective wavelength of laser. Each of the single-mode optical fibers are stripped of their coating and arranged in a triangular configuration. An achromatic doublet (not shown), or other suitable collimating optic 530 may be used to collimate the light from the fiber bundle.

Due to the lateral offset of the light in the focal plane, each of the beams will slightly diverge and will be focused by the lens 535 at a different position in the focal plane of the catch head optic, increasing linearly with increasing distance between the pitch and catch heads. This lateral offset is illustrated by the divergence cones 515, 520, 525 originating from each of the cores respectively. The optical paths X-X, Y-Y, and Z-Z correspond to the beams of each of the three cones 515, 520, 525. Therefore, when focused by the lens 535, each beam is focused to a different point in space. For example, the beam originating from the uppermost fiber of the triangular bundle configuration, having divergence cone 515, and taking optical path X-X, is focused at a position indicated by point 540. The beam from the lower right fiber, having divergence cone 520, and traveling along optical path Y-Y, is focused at the position indicated by point 545. The beam from the lower left fiber, having divergence cone 525, and traveling along optical path Z-Z, is focused at the position indicated by point 550. Thus, when the beams reach the catch head 555, the catch head 555 must be aligned to receive the signal at the points 540, 545, 550 corresponding to the transmitted beam. In various embodiments, the catch head may include the auto-alignment system described in the '755 patent, and as described in further detail with respect to FIG. 6 below. In some embodiments, the catch head 555 may simply include a photodetector 560 for detecting each of the transmitted wavelengths, thus the catch head 555, pitch head (not shown), or both are adjusted such that the beams are received by the sensor. Thus, the photodetector 560 must be positioned such that the photodetector 560 will receive the respective beams at point 540 during the window of time that it is transmitted, at point 545 during the time window that it is transmitted, and at point 550 at the appropriate time windows.

In an alternative set of embodiments, the beams may be directed towards a respective fiber in the catch head. For example, in some embodiments, the catch head may include a catch side fiber bundle assembly, where the catch head 555, catch side fiber bundle assembly, pitch head (not pictured), pitch side fiber bundle assembly 505, or a combination these elements must be aligned by the auto-alignment system such that the each wavelength beam is received by a respective fiber core of the fiber bundle of the catch side fiber bundle assembly. For example, in some embodiments, the top most fiber of the catch side fiber bundle assembly may correspond to, or be the same type of fiber as, the top most fiber of the pitch side fiber bundle assembly 505. Similarly, the bottom left fibers may correspond to one another, and bottom right fibers may also correspond to one another.

Figure 6:
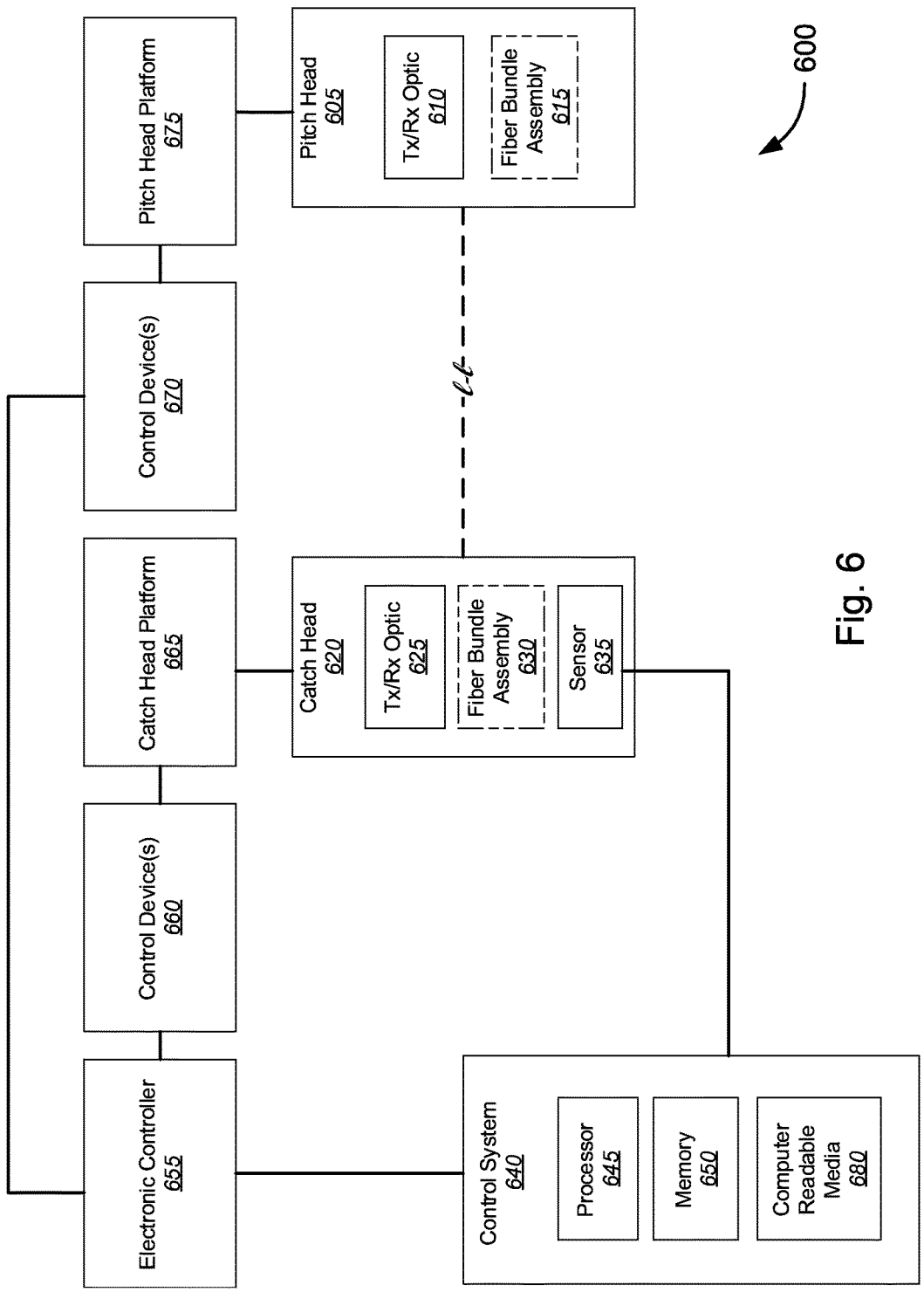
FIG. 6 is a block diagram of a control system as used in a widely spaced wavelength TDLAS system.

FIG. 6 is a system block diagram of an auto-alignment system 600 for a widely spaced TDLAS system. The auto-alignment system 600 includes a pitch head 605, coupled to a pitch head platform 675, and in optical communication with a catch head 620, the catch head 620 coupled to a catch head platform 665. Pitch head 605 transmits an optical signal to catch head 620 via optical path 1-1. The pitch head 605 includes transmitting optic 610, and, in various embodiments, may optionally include fiber bundle assembly 615. The catch head 620 includes receive optic 625, an optional fiber bundle assembly 630 (shown in phantom lines), and sensor 635.

The pitch head platform 675 is coupled to one or more control devices 670, and catch head platform 665 is coupled to one or more control devices 660. Each of the control devices 660, 670 are communicatively coupled to an electronic controller 655. The electronic controller 655 is coupled to the control system 640. The sensor 635 of catch head 620 is also communicatively coupled to the control system 640 providing measurement data to the control system 640 for feedback based alignment control among other calculations and functions based on the measured signals. In various embodiments, the sensor 635 includes a dual band detector as described above with respect to FIG.

2. The control system 640 includes processor 645, memory 650, and computer readable media 680. The control system may include various software elements and computer instructions which may be stored on a computer readable medium 680 and loaded into system memory 650. System memory 650 may include, without limitation, random access memory (RAM) or read-only memory (ROM), which can be programmable, flash-updateable, or the like.

Each catch and pitch head is attached respectively to catch and pitch head platforms 665, 675. The catch and pitch head platforms 665, 675 are adjustable along at least two axes of freedom. For example, in one set of embodiments, the catch and pitch head platforms may allow tip and tilt about axes orthogonal to the optical axis 1-1, and rotation about the optical axis 1-1. In further embodiments, the catch and pitch head platforms 665, 675 may also move laterally, along a plane orthogonal to the optical axis 1-1, and move forward and backward, transversely along the optical axis 1-1. Tip, tilt, rotation, lateral and on-axis movements may be actuated by one or more respective control devices 660, 670. The control devices 660, 670 include, without limitation, servo motors, stepper motors, pneumatic actuators, hydraulic actuators, or any other electro-mechanical means of actuation for adjusting the position of the catch and pitch head platforms 665, 675. According to another set of embodiments, each of the components of the pitch and catch heads 605, 620 may be controlled independently, with each component mounted on separate adjustable stages. For example, in various embodiments, any or all of the transmitting optic 610, fiber bundle assembly 615, pitch head 605, receiving optic 625, optional catch side fiber bundle assembly 630, photodetector 635, and catch head 620 may be mounted on independent adjustable stages.

The control devices 660, 670 may be controlled by an electronic controller 655. During system alignment, various embodiments call for the control system 640 to monitor the optical power of the received laser light that is detected by sensor 635. Misalignment will decrease the optical power of the received signal. During auto-alignment, the control system 640 measures the detected signal from sensor 635 and directs the electronic controller 655 to cause one or both of the control devices 660, 670 to move a predetermined displacement in one direction. The control system 640 then re-measures the detected signal. If the signal increases, then the control system 640 directs the electronic controller 655 to cause the control device 660, 670 to continue moving in steps in the same direction until the signal does not increase any further. The control system 640 will then direct the electronic controller 655 to cause the other control devices of the one or more control devices 660, 670 to move along an axis orthogonal to the previous axis. Tip, tilt, lateral, and transverse movements may be made in this manner to align the pitch and catch heads 605, 620. In this way, the sensor 635 provides feedback to the control system 640 for auto-alignment purposes. In other embodiments, the pitch and catch heads may be aligned along multiple axes simultaneously, in alternating fashion, or sequentially, one axis at a time. In some embodiments, the control system 640 may merely relay the measured signal levels to the electronic controller 655, with which the electronic controller 655 may then conduct the alignment procedure. In other embodiments, the control system 640 may directly send control signals to the control devices 660, 670 without need for electronic controller 655. In various embodiments, the control system 640 may move the catch head platform 665 and pitch head platform 675 independently or in a combined manner.

Due to the lateral offset of the fiber cores of the fiber bundle assembly (i.e. an offset in the focal plane), each of the transmitted beams will slightly diverge. Thus, when decollimated by the receiving optic 625, the beams will be focused at different points in space. Thus, when auto-aligned by the system, multiple alignments may be necessary corresponding to each of the signals from each of the cores of the fiber bundle. In some embodiments, the control system 640 may run the auto-alignment procedure for each wavelength beam corresponding to each respective fiber core. Thus, the catch head 620 must be aligned such that sensor 635 receives the corresponding wavelength beam from the pitch side fiber bundle assembly 615.

In various embodiments, the auto-alignment procedure may be conducted before actual operation, and alignment positions for each received wavelength beam may be stored by the electronic controller 655 and/or control system 640, and the catch head 620 may be adjusted to each of the stored positions corresponding to the transmitted wavelength beam. In other embodiments, the alignment of the catch head 620 may be adjusted in real-time as each beam is transmitted.

In one aspect, embodiments may employ the control system 640 to perform methods in accordance with various embodiments of the invention. According to a set of embodiments, some or all of the procedures of such methods are performed by the control system 640 in response to processor 645 executing one or more sequences of one or more instructions. The one or more instructions might be incorporated into an operating system and/or other code that may be contained in memory 650, such as an application program. Such instructions may be read into memory 650 from computer readable media 680, such as one or more of the storage device(s) (not pictured).

Alternative Dichroic Beam Combiner Architecture

Figure 7:
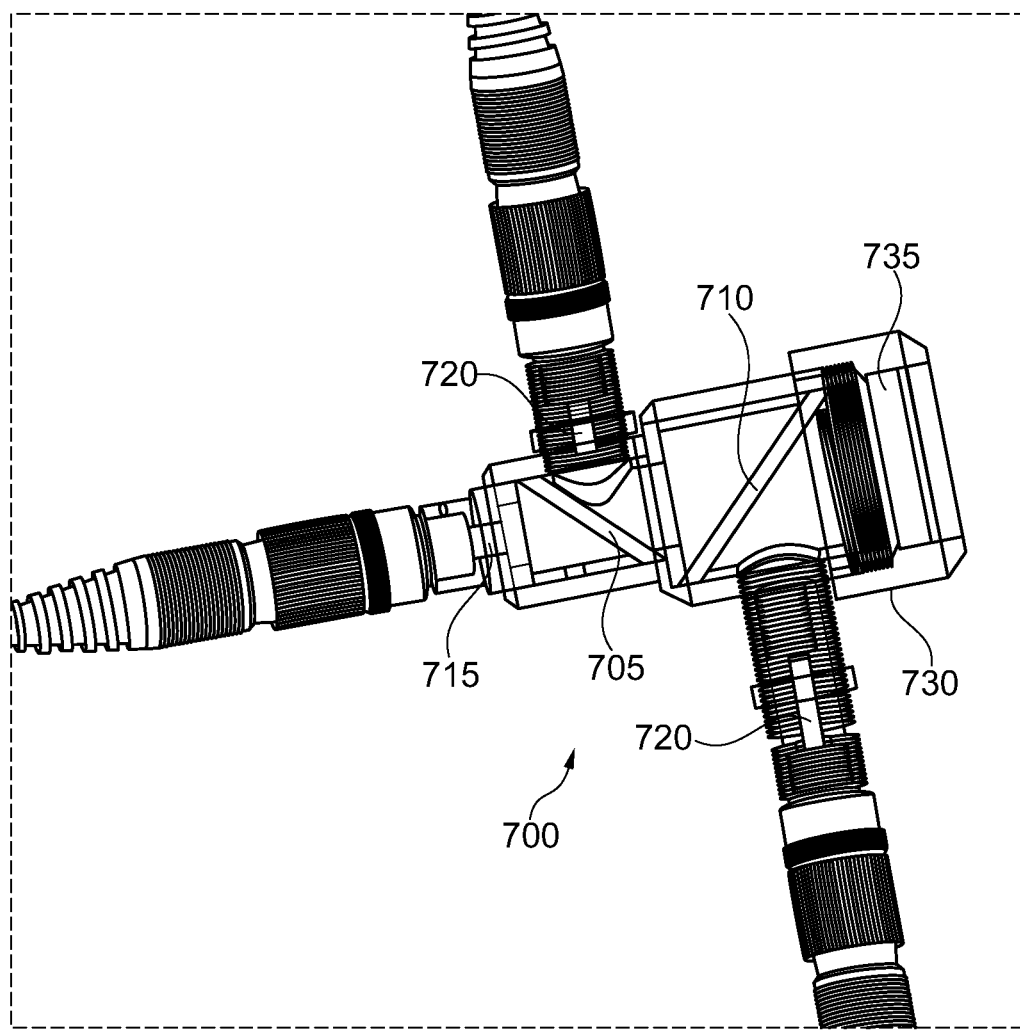
FIG. 7 illustrates a dichroic beam combiner for pitch or catch heads in a widely spaced wavelength TDLAS system.

FIG. 7 illustrates an alternative architecture for transmitting widely spaced wavelength beams, in single mode operation, from a single pitch head, and to a corresponding single catch head, with a dichroic beam combiner 700, in accordance with various embodiments. A dichroic beam combiner 700 is provided in each transmitting pitch head, catch head, or both the pitch and catch heads of a widely spaced wavelength TDLAS system.

Dichroic beam combiner 700 comprises a housing 730 having a first dichroic element 705 and a second dichroic element 710. Each of the dichroic elements 705, 710 acts as a dichroic beamsplitter or mirror that reflects light of a specific wavelength or range of wavelengths, while allowing light at other wavelengths to pass through. For example, according to one set of embodiments, the single-mode fiber 715 may be used to transmit 2330 nm wavelength light, single-mode fiber 720 is used to transmit 1350 nm light, and single-mode fiber 725 is used to transmit 760 nm light. Thus, the dichroic elements 705, 710 are selected to allow 2330 nm light to pass through, with dichroic element 705 reflecting light at 1350 nm, and dichroic element 710 reflecting light at 760 nm, but also allowing 1350 nm light to pass.

Thus, each wavelength of laser beam enters the dichroic beam combiner 700 via a respective single-mode fiber 715, 720, 725 appropriate for that wavelength, with each of the single-mode fibers 715, 720, and 725 optically coupled to the housing 730. The housing 730, single-mode optical fibers 715, 720, 725 and dichroic elements 705, 710 are configured and aligned to produce a wavelength-combined beam that is collimated through collimating lens 735 at an exit aperture of the housing 730.

Utilizing the dichroic beam combiner 700 architecture, either a TDM or WDM configuration may be utilized. For example, according to one set of embodiments, the various wavelengths of light of may be transmitted in an alternating manner, with only one wavelength of light transmitted at a given time. In embodiments utilizing a TDM configuration, the catch head may comprise a photodetector for directly receiving the transmitted signal. Alternatively, a corresponding catch side dichroic beam (de)combiner may be utilized. According to another set of embodiments, a WDM configuration may be utilized, where each wavelength of light is transmitted simultaneously. In such a configuration, a corresponding set of dichroic beam combiners may be utilized.

Where a pair of corresponding pitch and catch side dichroic beam combiners 700 is used, just as the pitch side dichroic beam combiner may be used to produce a wavelength-combined beam, the catch side dichroic beam combiner may be used to decombine the wavelength-combined beam. For example, in some embodiments, a pitch-side dichroic elements 705, 710 may be selected to allow 2330 nm light to pass through, with dichroic element 705 reflecting light at 1350 nm, and dichroic element 710 reflecting light at 760 nm, but also allowing 1350 nm light to pass. On the receiving-side, the dichroic elements 705, 710 may likewise be selected to allow 2330 nm light to pass through, but have dichroic element 710 on the catch side reflect light at 760 nm, while allowing light at 1350 nm and 2330 nm to pass through, dichroic element 705 on the catch side reflect light at 1350 nm, but allow light at 2330 nm to pass through.

In further embodiments, the dichroic beam combiners may also be utilized in combination with the fiber bundle assemblies as described with respect to the above embodiments, as well as the auto-alignment system described with respect to the fiber bundle assemblies.

While the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A system for widely spaced wavelength tunable diode laser absorption spectroscopy comprising:
at least a first and second tunable diode laser, the first tunable diode laser generating laser light at a first wavelength, the second tunable diode laser generating laser light at a second wavelength, wherein laser light of the first and second wavelengths cannot co-propagate in a single transverse mode with simultaneously high efficiency on a single-mode fiber;
a first fiber having a proximal end and a distal end, the first fiber optically coupled to the first tunable diode laser at the proximal end, the first fiber being a single mode optical fiber configured to carry light in the first wavelength;
a second fiber having a proximal end and a distal end, the second fiber optically coupled to the second tunable diode laser at the proximal end, the second fiber being a single mode optical fiber configured to carry light in the second wavelength;
a fiber bundle comprising the distal ends of at least the first and second fibers, wherein the distal ends of the first and second fibers are stripped of their respective coatings, and wherein a first fiber optic core of the first fiber and a second fiber optic core of the second fiber are arranged with their claddings adjacent to each other forming a bundled configuration;
one or more pitch heads comprising a transmitting optic, the transmitting optic optically coupled to the first and second tunable diode lasers via the distal ends of the first and second fibers of the fiber bundle, the pitch head configured to project respective beams of laser light from the first fiber optic core and the second fiber optic core, wherein the pitch head is oriented to project the respective beams from each of the first and second fiber optic cores through a measurement zone;
one or more sensors, each sensor comprising respectively at least one photodetector, each of the at least one photodetector configured to detect an optical power of light in the first and second wavelengths; and
one or more catch heads located across the measurement zone by a select distance from the one or more pitch heads, each of the one or more catch heads in optical communication with a respective pitch head of the one or more pitch head to receive the respective beams of the first and second fiber optic cores and direct the respective beams onto at least one of the one or more sensors.

2. The system of claim 1, wherein at least one of the one or more catch heads further comprises:
a receiving optic; and
at least one of the one or more sensors, respectively;
wherein at least one of the transmitting optic or the receiving optic is configured to direct the respective beams onto the at least one of the one or more sensors.

3. The system of claim 1 further comprising:
a third tunable diode laser generating laser light at a third wavelength;
a third fiber having a proximal end and a distal end, the third fiber optically coupled to the third tunable diode laser at the proximal end, the third fiber being a single mode optical fiber configured to carry light in the third wavelength;
wherein the fiber bundle further comprises the distal end of the third fiber, wherein the distal end of the third fiber is stripped of its coating, and wherein a third fiber optic core of the third fiber is arranged with its cladding adjacent to at least one of the first or second fiber optic cores forming part of the bundled configuration; and
wherein each of the at least one photodetector is configured to detect an optical power of light in the third wavelength.

4. The system of claim 3, wherein the bundled configuration is a triangular configuration of the first, second, and third fiber optic cores.

5. The system of claim 1, wherein the outputs of the first and second tunable diode lasers are switched according to a time-division multiplexing scheme, wherein laser light in only one of either the first or second wavelengths is projected by each of the one or more pitch heads at a given time.

6. The system of claim 1 further comprising a first optical switch coupled to the distal end of the first fiber, and a second optical switch coupled to the distal end of the second fiber, wherein the first and second optical switch are configured to switch their outputs serially between each of the one or more pitch heads.

7. The system of claim 1 further comprising a plurality of beam splitters coupled to the respective distal ends of the first and second fibers, wherein the plurality of beam splitters are configured to provide light in parallel to each of the one or more pitch heads.

8. The system of claim 1, wherein the first wavelength is about 760 nanometers, and the second wavelength is about 2330 nanometers.

9. The system of claim 1 further comprising:
one or more pitch head platforms, each of the one or more pitch head platforms coupled respectively to each of the one or more pitch heads, wherein the one or more pitch head platforms or each associated transmitting optic or pitch head are adjustable along at least two axes of freedom;
a plurality of control devices coupled respectively to each of the one or more pitch head platforms, or each associated transmitting optic or pitch head, wherein the control devices are operable to actuate each respective pitch head platform, or each associated transmitting optic or pitch head in at least one of the at least two axes of freedom;
an electronic controller in communication with the plurality of control devices and configured to supply control signals to each of the plurality of control devices; and
a control system configured to align a pitch head under alignment, of the one or more pitch heads, with a corresponding catch head of the one or more catch heads, wherein the control system causes an at least one control device of the plurality of control devices coupled to a pitch head platform or each associated transmitting optic or pitch head of the pitch head under alignment to adjust the position of the pitch head based at least in part on measurements received from the photodetector of a corresponding catch head of the pitch head under alignment.

10. The system of claim 9 further comprising:
one or more catch head platforms, each of the one or more catch head platforms having a receiving optic coupled respectively to each of the one or more catch heads, wherein the one or more catch head platforms or each associated receiving optic or catch head are adjustable along at least two axes of freedom;
wherein the plurality of control devices are coupled respectively to each of the one or more catch head platforms, or each associated receiving optic or catch head, wherein the control devices are operable to actuate each respective catch head platform or each associated receiving optic or catch head in at least one of the at least two axes of freedom; and
wherein the control system is configured to align a catch head, of the one or more catch heads, under alignment with a corresponding pitch head of the one or more pitch heads, wherein the control system causes an at least one control device of the plurality of control devices coupled to a catch head platform of the catch head under alignment or each associated receiving optic of the catch head under alignment or the catch head under alignment to adjust the position of the catch head based at least in part on measurements received from a sensor of the one or more sensors of the corresponding catch head under alignment.

11. A pitch head for widely spaced wavelength tunable diode laser absorption spectroscopy comprising:
a housing configured to optically couple with a fiber bundle, the fiber bundle comprising distal ends of at least a first and second input fibers, wherein the first input fiber is a single mode fiber that carries laser light at a first wavelength and the second input fiber is a single-mode fiber that carries laser light at a second wavelength, wherein laser light of the first and second wavelengths cannot co-propagate in a single transverse mode with simultaneously high efficiency on a single-mode fiber;
wherein the distal ends of at least the first and second input fibers are stripped of their respective coatings, and wherein a first fiber optic core of the first input fiber, and a second fiber optic core of the second input fiber are arranged with their claddings adjacent to each other forming a bundled configuration; and
a transmitting optic configured to project respective beams of laser light from each of the at least first and second fiber optic cores, through a measurement zone;
wherein the housing is oriented such that the respective beams reach a catch head located across the measurement zone a select distance from the housing.

12. The pitch head of claim 11, wherein the fiber bundle further comprises a distal end of a third input fiber, wherein the third input fiber is a single mode fiber that carries laser light at a third wavelength, wherein the distal end of the third fiber is stripped of its coating, and wherein a third fiber optic core of the third input fiber is arranged with its cladding adjacent to the cladding of at least one of the first or second fiber optic cores forming part of the bundled configuration.

13. The pitch head of claim 12, wherein the bundled configuration is a triangular configuration of the first, second and third fiber optic cores.

14. The pitch head of claim 11, wherein the housing is coupled to a pitch head platform, wherein the pitch head platform is coupled to a pitch head with at least one of the pitch head platform, transmitting optic or pitch head being adjustable along at least two axes of freedom, wherein a control device is coupled to at least one of the pitch head platform, transmitting optic or pitch head, wherein the control device is operable to actuate the at least one of the pitch head platform, transmitting optic or pitch head in at least one of the at least two axes of freedom, and wherein a control system is configured to align the pitch head with a corresponding catch head, wherein the control system causes the control device to adjust the position of the at least one of the pitch head platform, transmitting optic or pitch head at least in part on measurements received from a photodetector of the corresponding catch head.

15. The pitch head of claim 11, wherein laser light from the first and second input fibers are switched according time-division multiplexing scheme, wherein laser light in only one of either the first or second wavelengths is projected at a given time.

16. The pitch head of claim 11, wherein the first wavelength is about 760 nanometers, and the second wavelength is about 2330 nanometers.

17. A method for widely spaced wavelength tunable laser diode laser spectroscopy comprising:
- generating a first laser beam of a first wavelength;
- generating a second laser beam of a second wavelength;
- carrying the first laser beam on a first single-mode optical fiber and the second laser beam on a second single-mode optical fiber, wherein laser light of the first and second wavelengths cannot co-propagate in a single transverse mode with simultaneously high efficiency on a single-mode fiber;
- stripping distal ends of the first and second single-mode optical fiber of their respective coatings;
- arranging a first fiber optic core of the first single-mode optical fiber with its cladding adjacent to the cladding of a second fiber optic core of the second single-mode optical fiber forming a bundled configuration;
- forming a fiber bundle from the bundled configuration of the first and second fiber optic cores;
- transmitting, with a pitch head, respective beams of laser light, from each of the first and second fiber optic cores of the fiber bundle, through a measurement zone;
- receiving each respective beam at a catch head located across the measurement zone a select distance from the pitch head;
- detecting, at the catch head, an optical power of light in each of the first and second wavelengths; and
- determining a concentration of targeted species having an absorption line at the first and second wavelengths.

18. The method of claim 17 further comprising:
- adjusting one or more combustion parameters based on the relative concentration of the targeted species in the measurement zone.

19. The method of claim 17 further comprising:
- adjusting an orientation of the pitch or catch head based at least in part on the detected optical power of laser light.

20. The method of claim 17, further comprising switching the output of the first and second laser beams according to a time-division multiplexing, wherein laser light in only one of either the first or second wavelengths is transmitted at a given time.

* * * * *